(12) United States Patent
Cui et al.

(10) Patent No.: US 10,854,331 B2
(45) Date of Patent: Dec. 1, 2020

(54) PROCESSING A QUERY USING TRANSFORMED RAW DATA

(71) Applicant: Hewlett Packard Enterprise Development LP, Houston, TX (US)

(72) Inventors: Henggang Cui, Palo Alto, CA (US); Kimberly Keeton, Palo Alto, CA (US); Indrajit Roy, Palo Alto, CA (US); Krishnamurthy Viswanathan, Mountain View, CA (US); Haris Volos, Palo Alto, CA (US)

(73) Assignee: Hewlett Packard Enterprise Development LP, Houston, TX (US)

( * ) Notice: Subject to any disclaimer, the term of this patent is extended or adjusted under 35 U.S.C. 154(b) by 380 days.

(21) Appl. No.: 15/522,246

(22) PCT Filed: Oct. 26, 2014

(86) PCT No.: PCT/US2014/062305
§ 371 (c)(1),
(2) Date: Apr. 26, 2017

(87) PCT Pub. No.: WO2016/068829
PCT Pub. Date: May 6, 2016

(65) Prior Publication Data
US 2017/0322987 A1    Nov. 9, 2017

(51) Int. Cl.
| *G06F 16/2453* | (2019.01) |
| *G16H 40/63* | (2018.01) |
| *G06F 16/25* | (2019.01) |
| *G06F 17/14* | (2006.01) |
| *G06F 17/18* | (2006.01) |

(52) U.S. Cl.
CPC ......... *G16H 40/63* (2018.01); *G06F 16/2453* (2019.01); *G06F 16/254* (2019.01); *G06F 17/148* (2013.01); *G06F 17/18* (2013.01)

(58) Field of Classification Search
CPC ..... G06F 16/2453; G06F 17/18; G06F 17/148
See application file for complete search history.

(56) References Cited

U.S. PATENT DOCUMENTS 6,424,687 B1 * 7/2002 Tian .................. H03H 17/02
327/151
6,694,311 B1 * 2/2004 Smith ................ G06F 16/2264
(Continued)

FOREIGN PATENT DOCUMENTS

WO    WO-2014088903    6/2014

OTHER PUBLICATIONS

Charles Johnson, "From Research to Practice: Experiences Engineering a Production Metadata Database for a Scale Out File System", Proceedings of the 12th Usenix Conference on File and Storage Technologies (FAST '14), Santa Clara, CA, Feb. 17-20, 2014, (9 pages).

(Continued)

*Primary Examiner* — Kris E Mackes
(74) *Attorney, Agent, or Firm* — Trop, Pruner & Hu, P.C.

(57) ABSTRACT

A transformation on raw data is applied to produce transformed data, where the transformation includes at least one selected from among a summary of the raw data or a transform of the raw data between different domains. In response to a query to access data, the query is processed using the transformed data.

20 Claims, 3 Drawing Sheets

APPLY A TRANSFORMATION ON RAW DATA TO PRODUCE TRANSFORMED DATA FOR EACH TIME WINDOW OF MULTIPLE TIME WINDOWS — 202

IN RESPONSE TO A QUERY TO ACCESS DATA, PROCESS THE QUERY USING THE TRANSFORMED DATA IN AT LEAST A SUBSET OF THE MULTIPLE WINDOWS — 204

(56) References Cited

U.S. PATENT DOCUMENTS

| | | |
|---|---|---|
| 8,862,537 B1 | 10/2014 | Kurtic et al. |
| 2010/0023546 A1 | 1/2010 | Silsby |
| 2011/0264633 A1 | 10/2011 | Koifman et al. |
| 2012/0102066 A1 | 4/2012 | Eronen et al. |
| 2012/0323617 A1* | 12/2012 | Papst .................. G06Q 10/063 705/7.11 |
| 2013/0318236 A1 | 11/2013 | Coates et al. |
| 2014/0032506 A1 | 1/2014 | Hoey et al. |
| 2014/0040433 A1 | 2/2014 | Russell et al. |
| 2014/0169469 A1* | 6/2014 | Bernal .................. H04N 19/57 375/240.16 |
| 2014/0172866 A1 | 6/2014 | Lin et al. |

OTHER PUBLICATIONS

Galen Reeves, "Managing Massive Time Series Streams with Multi-Scale Compressed Trickles", Publisher ACM, VLDB '09, Lyon, France, Aug. 24-28, 2009, (12 pages).

International Searching Authority, The International Search Report and the Written Opinion, PCT/US2014/062305, dated May 29, 2015, 13 Pages.

Lior Abraham, "Scuba: Diving into Data at Facebook", Proceedings of the VLDB Endowment, vol. 6, No. 11, LVDB Endowment 2150-8097/13/09, Articles Presented at The 39th International Conference on Very large Data Bases, Aug. 26-30, 2013; Riva del Garda, Trento, Italy, (11 pages).

Matei Zaharia, "Resilient Distributed Datasets: A Fault-Tolerant Abstraction for In-Memory Cluster Computing", University of California, Berkeley, Mar. 2012, (14 pages).

Sameer Agarwal, "BlinkDB: Queries with Bounded Errors and Bounded Response Times on Very large Data", arXiv:1203.5485v2 [cs.DB], Jun. 19, 2012, (16 pages).

Abadi, D.J. et al.; "Aurora: a New Model and Architecture for Data Stream Management"; 2003; 20 pages.

Buevich, M. et al.; "Respawn: a Distributed Multi-resolution Time-series Datastore"; Oct. 7, 2013; 10 pages.

* cited by examiner

PROCESSING A QUERY USING TRANSFORMED RAW DATA

BACKGROUND

Data can be stored in a data store, such as in a structured database to store data structures (e.g. tables) according to a specific database schema, or in an unstructured data store in which data is stored in an unstructured manner. Queries can be submitted to access data in a data store. The access of data can include reading data, updating data, adding data, or deleting data.

BRIEF DESCRIPTION OF THE DRAWINGS

Some implementations are described with respect to the following figures.

DETAILED DESCRIPTION

Figure 1:
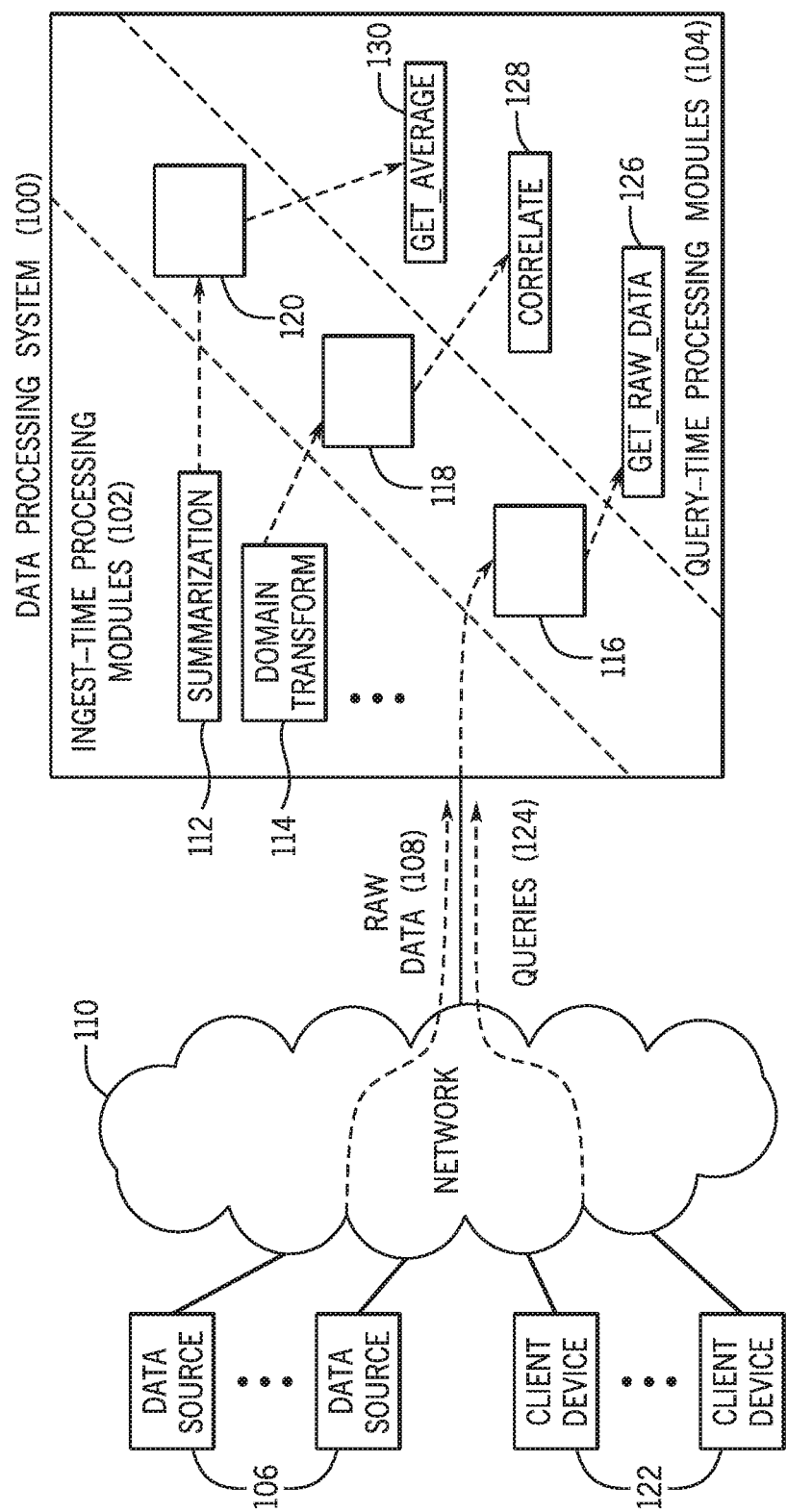
FIG. 1 is a block diagram of an example arrangement according to some implementations.

Massive amounts of raw data can be collected and stored in a data store (or multiple data stores). In some cases, a data store can be distributed across a number of computing nodes. "Raw data" can refer to data received from a data source, where a data source can refer to any entity (hardware entity or machine-readable instructions) that is able to produce data for output. In some cases, raw data can be data produced by measurement devices (e.g. sensors, etc.). In other cases, raw data can be computed from other data.

As examples, data sources can include sensors that are distributed across an information technology (IT) infrastructure (e.g. a data center, a cloud infrastructure, etc.) to collect measurement data regarding various components of the IT infrastructure. The IT infrastructure can include various types of components, including user devices, storage systems, communication nodes, server computers, and so forth. The sensors can be used to collect metrics that relate to various characteristics of the infrastructure, such as metrics relating to performance, loading, faults, and so forth. As examples, the metrics collected can include a number of processor accesses, a number of memory accesses, a number of disks accesses, a number of invocations of machine-readable instructions, processor loading, computer loading, storage capacity remaining, network bandwidth used, and so forth.

In a healthcare setting, data sources can include monitoring devices to monitor health metrics for patients, such as electrocardiography data, blood pressure data, patient imaging data, and so forth. In other settings, other types of raw data can be collected.

In some implementations, the collected raw data can be in the form of time series data, where the raw data is made up of a sequence of data points at respective times.

The performance of analytics on a large collection of data, including time series data, can be resource intensive. Examples of analytics that can be performed on collected data include calculating statistics (e.g. an average, mean, minimum, maximum, sum, count, etc.) of data values. In other examples, other analytics that can be performed data can include more complex calculations such as correlations, convolutions, frequency domain transformations (to transform data from a time domain to a frequency domain), modeling (such as auto-regressive or AR modeling), and so forth.

Due to the large amount of raw data, the raw data may be stored on relatively slow storage devices, such as disk-based storage devices. As a result, applying analytics on such raw data would involve accessing the raw data on the relatively slow storage devices, which increases the time to perform analytics on the raw data. Due to slow response times of the relatively slow storage devices, real-time analytics may not be possible. Real-time analytics refers to analysis of raw data that is performed as the raw data is received.

Analytics on data can be performed for various purposes, such as to find hotspots in an IT infrastructure (components in the IT infrastructure that are unusually loaded as compared to other components), faulty components in the IT infrastructure, health anomalies for patients, and other purposes.

In accordance with some implementations, techniques or mechanisms are provided to perform more efficient analytics on a collection of raw data, which can be time series data in some implementations. The analytics is performed by a data processing system, which can be implemented on a single computer or on a distributed arrangement of computers. The data processing system includes data storage resources to store data, and data processing resources to apply processing on data.

The data processing system is able to perform the following types of processing: (1) ingest-time processing, and (2) query-time processing. Ingest-time processing and query-time processing are combined to enable more efficient analytics on data. Ingest-time processing refers to processing on raw data ingested (received) by the data processing system. Query-time processing refers to processing on data (raw data and/or transformed data) performed in response to a query to access data.

An example data processing system 100 is shown in FIG. 1, which includes ingest-time processing modules 102 for performing ingest-time processing, and query-time processing modules 104 for performing processing in response to queries. As shown in FIG. 1, data sources 106 output raw data 108 that is ingested by the data processing system 100. The raw data 108 is communicated over a network 110 to the data processing system 100. The network 110 can include any or some combination of electrical links, optical paths, and wireless links.

As the raw data 108 is ingested by the data processing system 100, at least one module of the ingest-time processing modules 102 can apply ingest-time transformation on the ingested raw data 108. The ingest-time transformation can transform raw data for each time window of multiple time windows. More specifically, the ingest-time transformation can apply a transformation on raw data in a first window to produce transformed raw data for the first time window, apply a transformation on raw data in a second window to produce transformed raw data for the second time window, and so forth. The transformations can be continually applied as new raw data is received.

The ingest-time processing modules 102 include a summarization module 112 that produces a summary of raw data. A summary of raw data can include any or some combination of the following, as examples: a minimum of data values, a maximum of data values, a sum of data values, a count of data values, pairwise dot products of vectors, data modeling, and other summary operations. Although just one summarization module 112 is shown in FIG. 1, it is noted that there can be multiple summarization modules.

An example of data modeling can include autoregressive (AR) modeling, which can produce a model that represents time-varying processes. The AR model can be characterized using AR coefficients that are derived from raw data. The AR coefficients can be considered a summary of the raw data. Another example of data modeling can include an AR moving-average (ARMA) statistical modeling. More generally, a model derived from raw data can be considered a summary of the raw data.

The ingest-time processing modules 102 further include a domain transform module 114, which can transform raw data in a first domain into transformed data in a second domain. As examples, the first domain can include a time domain, and the second domain can include a frequency domain. In other examples, transformation can be performed between other types of domains. An examples of a domain transform includes a fast Fourier transform (FFT), which can transform raw data from a time domain (or space domain) to a frequency domain, or vice versa. Another example of a domain transform includes a wavelet transform that transforms data between time and frequency domains. Other examples of domain transforms can be provided. Although just one domain transform module 114 is shown in FIG. 1, it is noted that there can be multiple domain transform modules.

In addition to the summarization module 112 and the domain transform module 114, the ingest-time processing modules 102 can further include other transformation modules, such as a frequency filtering module, a down-sampling module, a data cleansing module, a data cloning module, a data adding module, and a data multiplying module. A frequency filtering module can include a low-pass filtering module (which can remove data samples at frequencies less than a threshold frequency), a high-pass filtering module (which can remove data samples at frequencies higher than a threshold frequency), a bandpass filter (which can pass data samples having frequencies within a specified range, but removes data samples outside the specified range), or a band-stop filter (which can pass data samples at all frequencies but those within a specified range). Note that a frequency filter can be applied after a domain transform has been performed on raw data from the time domain to the frequency domain.

Down-sampling of data can refer to selecting a subset less than all of a collection of data samples. Down-sampling can be performed on the raw data 108 (in the time domain), or on transformed data (e.g. transformed data in the frequency domain or another domain).

Data cleansing of data can refer to any operation that attempts to identify and fix any issues in data, such as to calculate interpolated data samples that are missing from incoming data, fix errors in the data, and so forth. Data cleansing can be applied on data in the time domain or in the frequency domain, or in another domain.

Data cloning can refer to copying (cloning) data. Data adding can refer to adding data to another value. Data multiplying can refer to multiplying data to another value.

The data processing system 100 can store data in various data structures 116, 118, and 120. For example, the data structure 116 can store the raw data 108 ingested by the data processing system 100. The data structure 118 can store transformed data produced by the domain transform module 114. The data structure 120 can store summary data produced by the summarization module 112. Although just three data structures are shown in FIG. 1, it is noted that there can be more data structures. The data structures can include tables or other types of data structures for storing data. The data stored in the data structures 116, 118, and 120 can be in respective time windows.

The data structures 116, 118, and 20 can be stored on storage resources of the data processing system 100. The storage resources can include memory (which can be implemented with memory devices such as dynamic random access memory or DRAM devices, flash memory devices, and so forth), and persistent storage (which can be implemented with disk-based storage devices or other solid state persistent storage).

The query-time processing modules 104 include various modules that are able to perform processing on data in response to queries 124 received from client devices 122 over the network 110. Examples of the client devices 122 include computers (e.g. desktop computers, tablet computers, notebook computers, server computers, etc.), handheld devices, and so forth. In response to a query 124, at least one of the query-time processing modules 104 is invoked to perform query-time processing. The query-time processing performed in response to a query 124 can use data in any one or multiple data structures 116, 118, and 120.

The query-time processing can use data in specific time windows. For example, if a query seeks to compute an average of data values in the past 24 hours, then the query-time processing can employ data in time window(s) in the past 24 hours from at least one of the data structures 116, 118, and 120. For example, the average can be computed by using sum and count values produced by summarization modules 112 in a subset of time windows.

The query-time processing modules 104 can include the following modules, as examples: a Get_Raw_Data module 126 (to access selected raw data in the data structure 116), a Correlate module 128 (to correlate data), and a Get_Average module 130 (to compute an average of data). In other examples, other query-time processing modules 104 can include a module to perform convolution on data, a module to determine a distribution of data, a module to compute a dot product of time series data, or other operations.

An example scenario can involve analysis of patient data in a healthcare setting. For example, the domain transform module 114 of the ingest-time modules 102 can transform input raw data (containing monitored health metrics) from a time domain to a frequency domain, and following the transform to the frequency domain, a filter module of the ingest-time modules can filter out the high-frequency components and store just the low-frequency components with fewer samples. If most of the energy of a signal represented by the raw data is contained in the low frequency portion of the frequency spectrum (the high-frequency components may be mainly noise, for example), this approach allows for retention of most of the information of the original data with fewer samples and hence can reduce query-time processing. At query time, a query on raw data can be automatically translated into a query on a corresponding transformed data. In the foregoing example, a query on raw patient data can be translated to a query on the filtered data that includes just low-frequency components.

Figure 2:
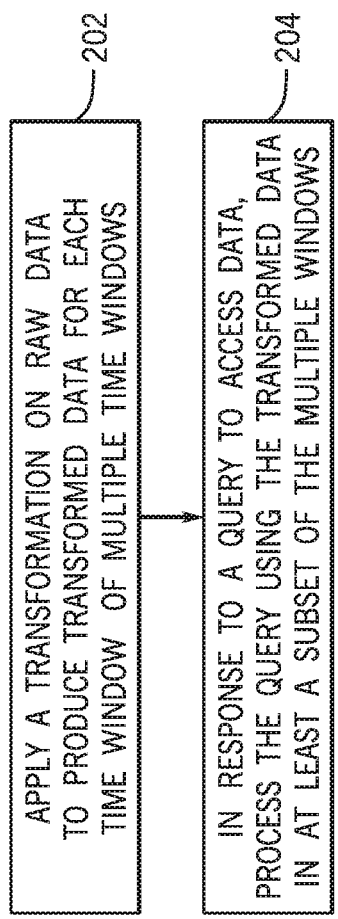
FIG. 2 is a flow diagram of an example process according to some implementations.

FIG. 2 is a flow diagram of a process according to some implementations, which can be performed by the data processing system 100. The process applies (at 202) a transformation on ingested raw data (e.g. 108 in FIG. 1) to produce transformed data for each time window of multiple time windows.

Raw data is ingested in time windows, where each time window corresponds to one or multiple metrics recorded in a time range. Transformation functions are applied on raw data in each time window. Transformations to be applied can be specified by users or can be automatically determined.

In some implementations, the transformation on the raw data for a first time window of the multiple time windows is independent of the transformation on the raw data for a second time window of the multiple of time windows. More specifically, the transformation applied in each of the time windows can be independent of the transformation applied in others of the time windows.

In alternative implementations, stateful transformations can be applied. With a stateful transformation, a state is preserved from one time window to another time window. For example, to perform anomaly detection, a count can be maintained of the number of times a particular condition occurs, and a flag can be raised if a threshold is reached. Other examples include pattern matching and rule-based event processing. More generally, with a stateful transformation, a state is determined based on applying of a transformation on raw data for multiple time windows.

The output data of a transformation may have different cardinality than the input data to the transformation. A cardinality of data can refer to a number of rows of data or some other indication of a size of the data. The relationship between input and output cardinalities falls into one of the following categories: a) one-to-one transformations, such as clone, add, and multiply; b) many-to-one summary transformations, such as minimum, maximum, and summation; and c) many-to-many transformations such as low-pass filtering, down-sampling, FFT, wavelet transform, and data cleansing.

As further shown in FIG. 2, in response to a query to access data, the query can be processed (at 204) using the transformed data (and possibly also using raw data) in at least a subset of the multiple time windows.

Figure 3:
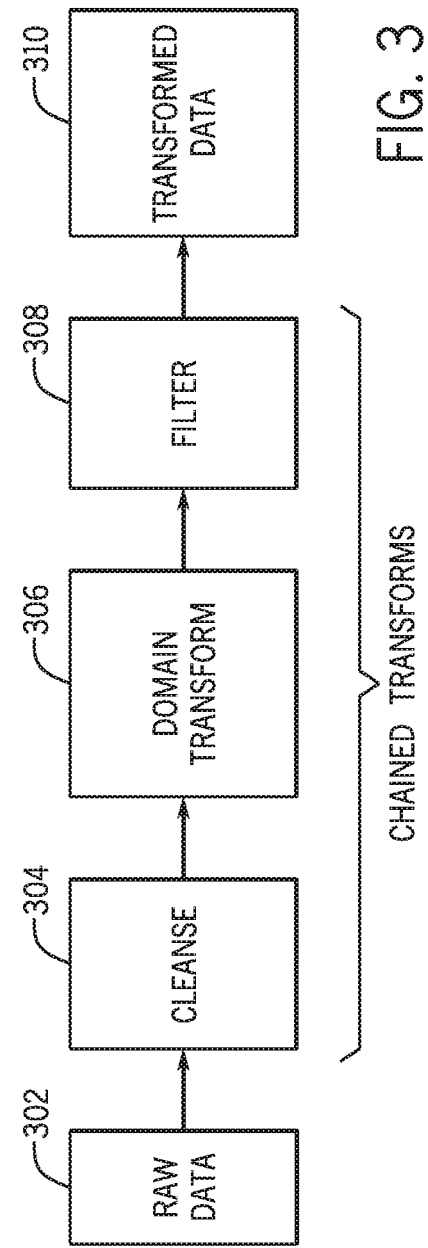
FIG. 3 is a block diagram of chained transforms according to further implementations.

In further implementations, chaining of multiple transformations can be performed. FIG. 3 shows an example of chaining multiple transforms. Raw data 302 is passed through a cleanse transform 304, in which any missing data values can be determined, such as by interpolation.

The chained transforms applies a domain transform 306 (e.g. FFT) to transform the cleansed data from the time domain to data in the frequency domain. The chained transforms further includes a filter transform 308 to filter out (remove or attenuate) data of specified frequency values.

The output of the filter transform 308 is transformed data 310 against which query processing can be applied.

By employing techniques or mechanisms according to some implementations, certain example benefits may be achieved. Ingest-time transformations can permit query-time speedups for certain queries on raw data, due to transformed data being smaller than the raw data and/or certain pre-computations being performed at the ingest stage (which means that such computations would not have to be performed at the query stage).

Additionally, pre-computing transformed data can reduce redundant query-time calculations. For example, if multiple queries use FFT transformed data or an AR model of the data, then the FFT transformed data or the AR model can be pre-computed once and used in processing for the multiple queries.

Further, certain transformed data can be compact enough that the transformed data of selected time windows can be stored in higher-speed memory, so that query processing can be performed using the data in the memory without having to access slower storage devices.

In some cases, transformations can be calculated without substantial overhead beyond the ingestion of un-transformed data. Additionally, due to the characteristics of certain metrics, queries on transformed data may not sacrifice query accuracy to obtain higher performance.

In response to a query, a query-time module (or multiple query-time modules) can be selected from the query-time processing modules 104 (FIG. 1) to automatically use the most suitable transformed data to answer the query. For example, a query for the average metric value over multiple windows can be calculated by querying the summation and count results for the requested windows.

A query submitted against the data of the data processing system 100 can be a real-time query or a historical query. A real-time query refers to a query that produces a result as data is received. A historical query involves accessing historical data (including historical transformed data as computed by the ingest-time processing modules 102) and possibly recently received data.

Processing a query using transformed data can result in some amount of error. For example, filtering data, down-sampling of data, or summarizing data can result in some amount of lost information, which can result in a query answer not being fully accurate if the query is processed using the transformed data.

In accordance with some implementations, a user or other entity can specify an error bound regarding a target quality of a query answer. The error bound can specify that an error in a query answer should not exceed some percentage value (e.g. error should be less than 10% or the query answer should be accurate to greater than 95%). The data processing system 100 can provide automatically tuned versions of a transformation that meet a particular guarantee on the quality of the query answer. For example, time domain data may be transformed into frequency domain data, and then a low-pass filter applied to retain only a fraction of the data samples (frequency components). Many signals contain significant energy for only a small fraction of the frequency components (e.g. 88% of the signal energy in the top 1% of frequency components), thus allowing a low-pass filtered representation of the data to closely approximate the original signal. An automatically tuned parameterization can choose what fraction of frequency domain components (data samples) to use based on a target signal energy, which is an example of a target quality of the query answer. For example, the target signal energy can specify that 90% of the signal energy is to be preserved. In response to the target signal energy, the data processing system 100 can choose a filter transform that preserves the corresponding amount of frequency components (top 1% of frequency components, top 5% of frequency components, etc.). In this way, the selected transformation to use for query processing can more meaningfully capture the target accuracy desired for a query.

As another example, wavelet transformed data can be used to summarize the raw data without losing too much information. In this example, the wavelet transformation calculates wavelet coefficients for each time window of ingested raw data. Based on a specified error bound, the K (K>1) largest wavelet coefficients are retained in the transformed data, where K is the minimum number of coefficients that are provided to satisfy the error bound. K coefficients can be much smaller in size than the corresponding raw data, so the transformed data is a compact representation of the raw data. At query time, a user or other entity can provide an error bound for each query. For example, a user can write a query such as "Find the time range within time 0 to 1000 that has the largest correlation with time 1000 to 1200, with error less than 15%." The data processing system 100 can then use a wavelet transformed data that has less than 15% error to answer the query.

Note that if the specified error bound is 0% (in other words, no error in the query answer is specified), then the query can be processed using the raw data.

Figure 4:
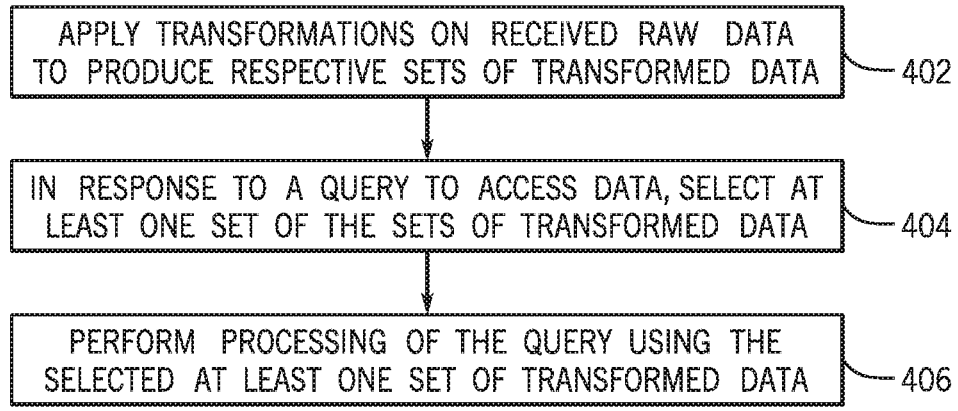
FIG. 4 is a flow diagram of another example process according to further implementations.

FIG. 4 is a flow diagram of another example process according to some implementations, which can be performed by the data processing system 100 of FIG. 1. The process of FIG. 4 applies (at 402) transformations on received raw data to produce respective sets of transformed data. The transformations can include a summarization of the raw data and a transform of the raw data between different domains (and possibly other transformations). The sets of transformed data can be stored in respective data structures (such as 118 and 120 in FIG. 1).

In response to a query to access data, at least one of the sets of transformed data is selected (at 404). The selection can be based on the operation sought by the query, and/or based on an error bound specified for the query. For example, if the query seeks an average of metric values, then a set containing summarized data can be selected. As another example, if the query seeks to detect an anomaly in patient data, then selected sets containing domain transformed data and filtered data can be selected.

Moreover, based on the specified error bound, the data processing system 100 can select use of the set of transformed data that can meet the specified error bound.

Next, the process of FIG. 4 performs (at 406) processing of the query using the selected at least one set of transformed data.

In further implementations, to improve performance for a query that is repeated numerous times, a query result for the query can be stored as transformed data, such that a subsequent invocation of the query can use the stored query result.

In additional implementations, the data processing system 100 can monitor query access patterns and query results, and the data processing system 100 can adapt transformations to be applied by the ingest-time processing modules 102 based on the monitored query access patterns and query results. The monitoring can indicate that certain new transformations should be applied. In other cases, the monitoring can indicate that certain existing transformations are infrequently used and can be dropped, so that the dropped transformations are no longer applied by the ingest-time processing modules 102. As examples, if the current transformations only store results for a 5% error bound, but most queries specify a 15% error bound, then a transformation can be added that supports 15% error bound since it will be more efficient than using the transformation results for the 5% error bound.

Figure 5:
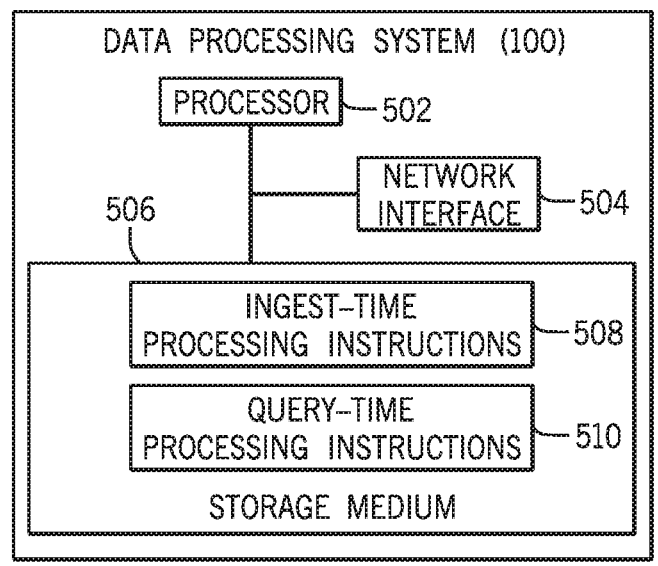
FIG. 5 is a block diagram of a data processing system according to some implementations.

FIG. 5 is a block diagram of an example data processing system 100 according to some implementations. The system 100 can be implemented on a computer or on a distributed arrangement of computers. The system 100 includes a processor (or multiple processors) 502. A processor can include a microprocessor, microcontroller, physical processor module or subsystem, programmable integrated circuit, programmable gate array, or another physical control or computing device.

The processor(s) 502 can be coupled to a network interface 504, which allows the data processing system 100 to communicate over a network (e.g. 110 in FIG. 1).

The processor(s) 502 can also be coupled to a non-transitory machine-readable or computer-readable storage medium (or storage media) 506. The storage medium (or storage media) 506 can be used to store data as well as machine-readable instructions. For example, the machine-readable instructions can include ingest-time processing instructions 508 and query-time processing instructions 510, to perform ingest-time processing and query-time processing, respectively, as discussed above.

The storage medium (or storage media) 506 can include one or multiple different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In the foregoing description, numerous details are set forth to provide an understanding of the subject disclosed herein. However, implementations may be practiced without some of these details. Other implementations may include modifications and variations from the details discussed above. It is intended that the appended claims cover such modifications and variations.

What is claimed is:
1. A method comprising:
applying, by a system comprising a processor, a transformation on raw data to produce first transformed data for a first time window of a plurality of time windows and second transformed data for a second time window of the plurality of time windows,
wherein the transformation of the first transformed data for the first time window produces a summary of the raw data in the first time window and the transformation of the second transformed data for the second time window produces the second transformed data in different domains in the second time window, and
wherein the application of the transformation of the first transformed data and the transformation of the second transformed data retains a fraction of the raw data;
calculating an interpolated data sample that is missing from the first transformed data and the second transformed data; and
in response to a query to access data at a query time, processing, by the system, the query using the first and second transformed data in at least a subset of the plurality of time windows,
wherein the first and second transformed data is a compact representation of the raw data and is stored in non-disk-based storage devices, and wherein the query is enabled to access the raw data, the interpolated data sample, the first transformed data, and the second transformed data absent transforming the data at the query time.

2. The method of claim 1, wherein applying the transformation comprises transforming the raw data in a first domain to the transformed raw data in a second, different domain.

3. The method of claim 2, wherein the first domain is a time domain, and the second domain is a frequency domain.

4. The method of claim 2, wherein the transformation comprises at least one from among a Fourier transform and a wavelet transform.

5. The method of claim 1, wherein the summary selected from among a sum of values of the raw data, a minimum of the values of the raw data, a maximum of the values of the raw data, a count of the values of the raw data, a product of the values of the raw data, and a model of the raw data.

6. The method of claim 1, wherein the summary comprising an auto-regressive model or an auto-regressive moving average model.

7. The method of claim 1, wherein the first time window of the plurality of time windows is independent of the second time window of the plurality of time windows.

8. The method of claim 1, further comprising:
determining a state based on applying the transformation on the raw data for multiple time windows of the plurality of time windows.

9. The method of claim 1, wherein applying the transformation comprises applying a chain of multiple transformations.

10. The method of claim 1, wherein applying the transformation is performed to satisfy a specified error bound for an answer of the query.

11. The method of claim 10, wherein the answer to the query is obtained by processing on the first or second transformed data and satisfies the specified error bound.

12. The method of claim 1 wherein the summary of the raw data in the first time window comprises deriving autoregressive (AR) modeling coefficients from the raw data.

13. The method of claim 1 wherein the transformation on the raw data further comprises down-sampling of the raw data.

14. The method of claim 1 wherein the transformation on raw data is a stateful transformation that preserves a state from the first time window to the second time window.

15. The method of claim 1 wherein the raw data includes monitored health metrics in a healthcare environment.

16. The method of claim 1 further comprising:
removing raw data at frequencies higher than a threshold frequency.

17. The method of claim 1 wherein the non-disk-based storage devices include solid state persistent storage.

18. A system comprising:
a network interface to receive raw data from at least one data source; and
at least one processor to:
apply a transformation on the raw data to produce first transformed data for a first time window of a plurality of time windows and a second transformed data for a second time window of the plurality of time windows,
wherein the transformation of the first transformed data for the first time window produces a summarization of the raw data in the first time window and the transformation of the second transformed data for the second time window produces the second transformed data in different domains in the second time window, and wherein the application of the transformation of the first transformed data and the transformation of the second transformed data retains a fraction of the raw data;

calculating an interpolated data sample that is missing from the first transformed data and the second transformed data; and in response to a query to access data at a query time, processing the query using the first and second transformed data in at least a subset of the plurality of time windows, wherein the first and second transformed data is a compact representation of the raw data and is stored in non-disk-based storage devices, and wherein the query is enabled to access the raw data, the interpolated data sample, the first transformed data, and the second transformed data absent transforming the data at the query time.

19. The system of claim 18, wherein the first or second transformed data is selected based on at least one criterion selected from among a specified error bound for the query or based on an operation sought by the query.

20. An article comprising at least one non-transitory machine-readable storage medium storing instructions that upon execution cause a system to:

apply a transformation on raw data to produce first transformed data for a first time window of a plurality of time windows and second transformed data for a second time window of the plurality of time windows, wherein the transformation of the first transformed data for the first time window produces a summary of the raw data in the first time window and the transformation of the second transformed data for the second time window produces the second transformed data in different domains in the second time window, and wherein the application of the transformation of the first transformed data and the transformation of the second transformed data retains a fraction of the raw data;

calculating an interpolated data sample that is missing from the first transformed data and the second transformed data; and in response to a query to access data at a query time, process the query using the first and second transformed data in at least a subset of the plurality of time windows, wherein the first and second transformed data is a compact representation of the raw data and is stored in non-disk-based storage devices, and wherein the query is enabled to access the raw data, the interpolated data sample, the first transformed data, and the second transformed data absent transforming the data at the query time.

* * * * *